United States Patent [19]
Paolizzi et al.

[11] Patent Number: 5,443,494
[45] Date of Patent: Aug. 22, 1995

[54] SUPPORT FOR BEARING AND POSITIONALLY ADJUSTING ELECTRODES OF PORTABLE BELT DEVICES FOR PASSIVE GYMNASTICS

[75] Inventors: Marco Paolizzi; Marco Valentini, both of Rimini, Italy

[73] Assignee: Vupiesse Italia S.A.S. Di Valentine E Paolizzi E.C., Rimini, Italy

[21] Appl. No.: 170,406

[22] Filed: Dec. 20, 1993

[30] Foreign Application Priority Data

Dec. 23, 1992 [EP] European Pat. Off. ......... 92830683.6

[51] Int. Cl.$^6$ .............................................. A61N 1/22
[52] U.S. Cl. ..................................... 607/149; 128/644
[58] Field of Search ...................... 607/148, 149, 115; 128/639, 644

[56] References Cited

U.S. PATENT DOCUMENTS 452,250  5/1991  Williams .............................. 607/149
3,881,495  6/1975  Pannozzo et al. .

FOREIGN PATENT DOCUMENTS 0483072  4/1992  European Pat. Off. .

*Primary Examiner*—Lee S. Cohen
*Assistant Examiner*—Brian M. Green
*Attorney, Agent, or Firm*—Dvorak and Traub

[57] ABSTRACT

In the invention, at least one electrode is placed in contact with a user's skin such that it transmits electric impulses produced by a current generator to the skin. The support comprises a projecting support element, supporting two electrodes rotatably connected to the belt device such as to rotate with respect to the belt device, so that the electrodes can be positioned longitudinally or transversally to the device, correspondingly to the development direction of a muscle to be stimulated.

8 Claims, 3 Drawing Sheets

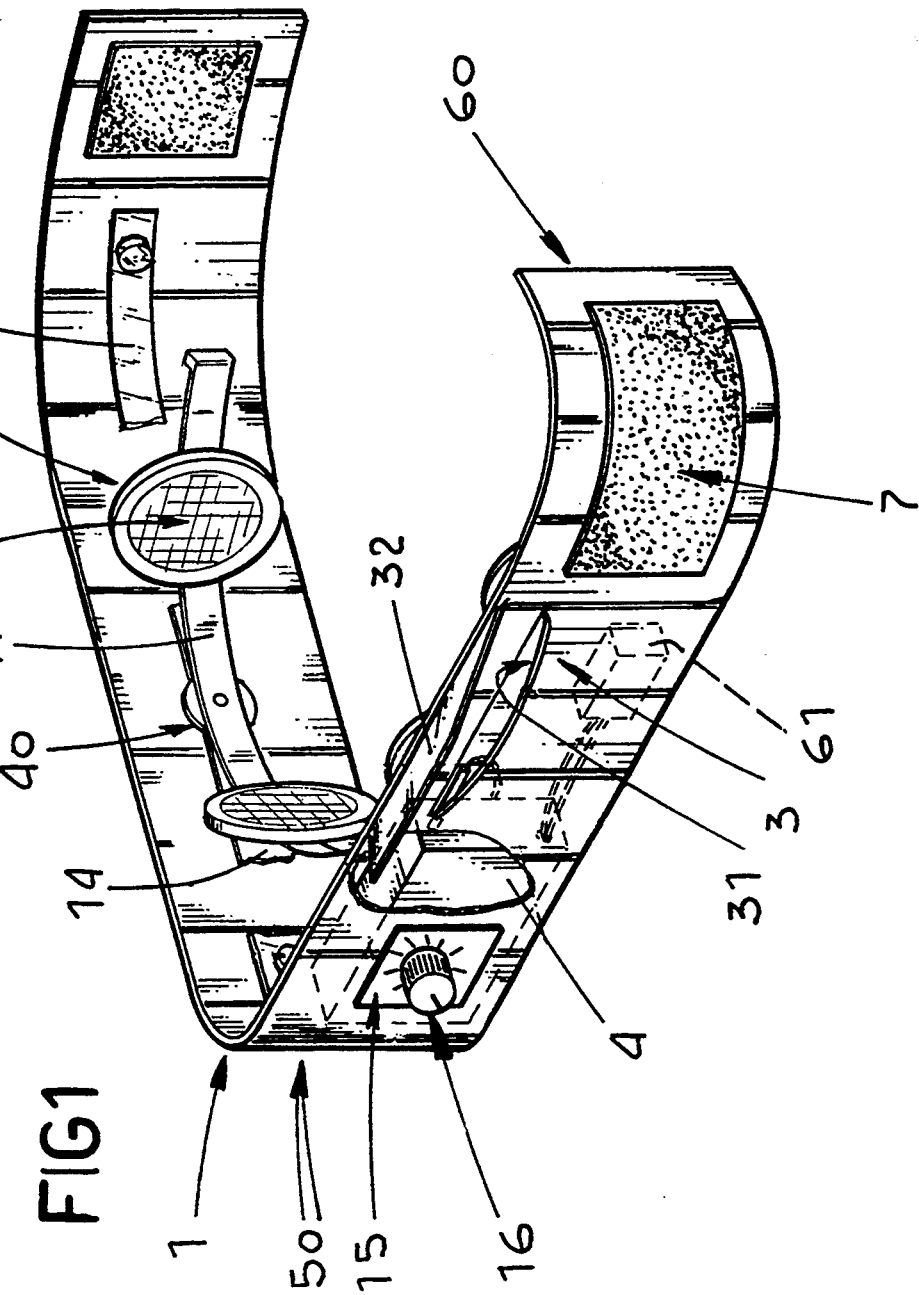

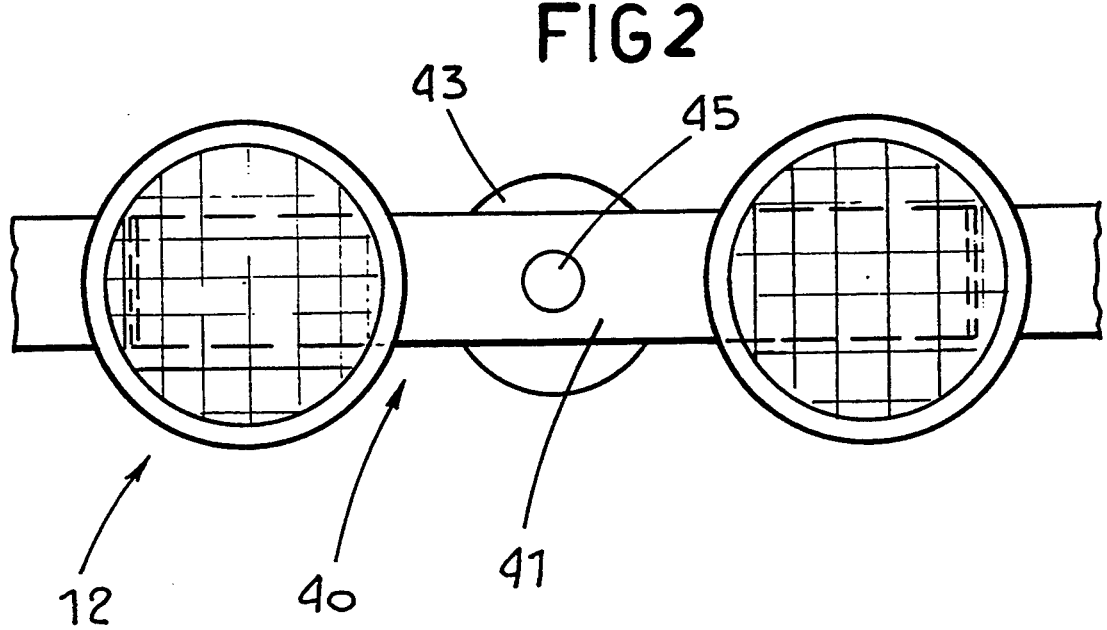
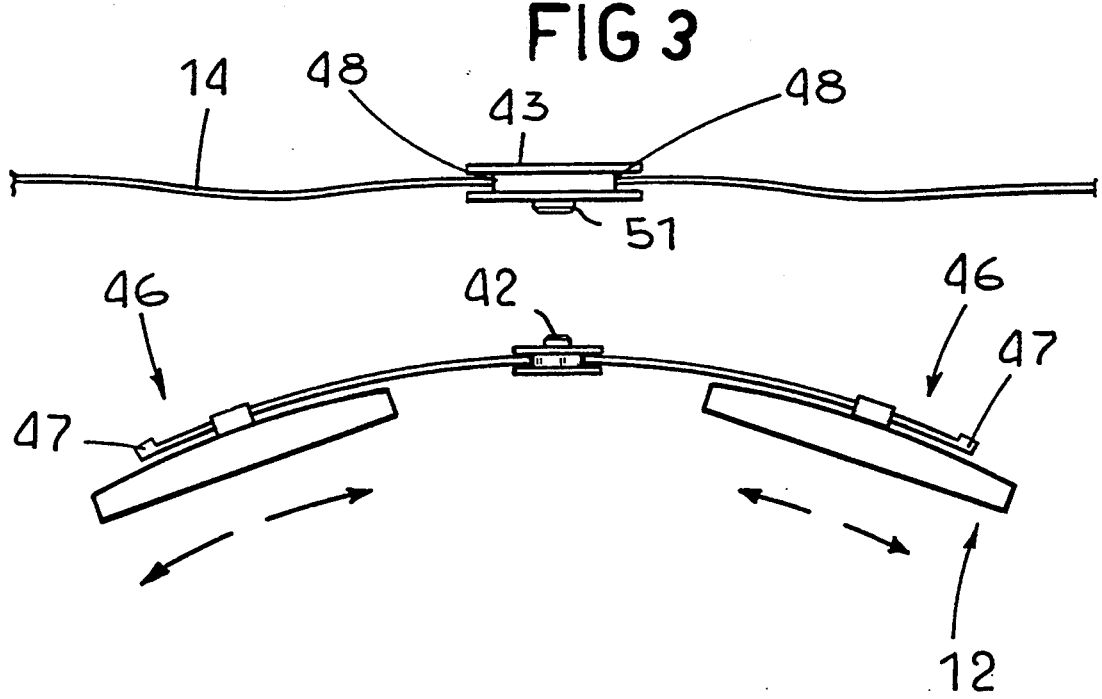

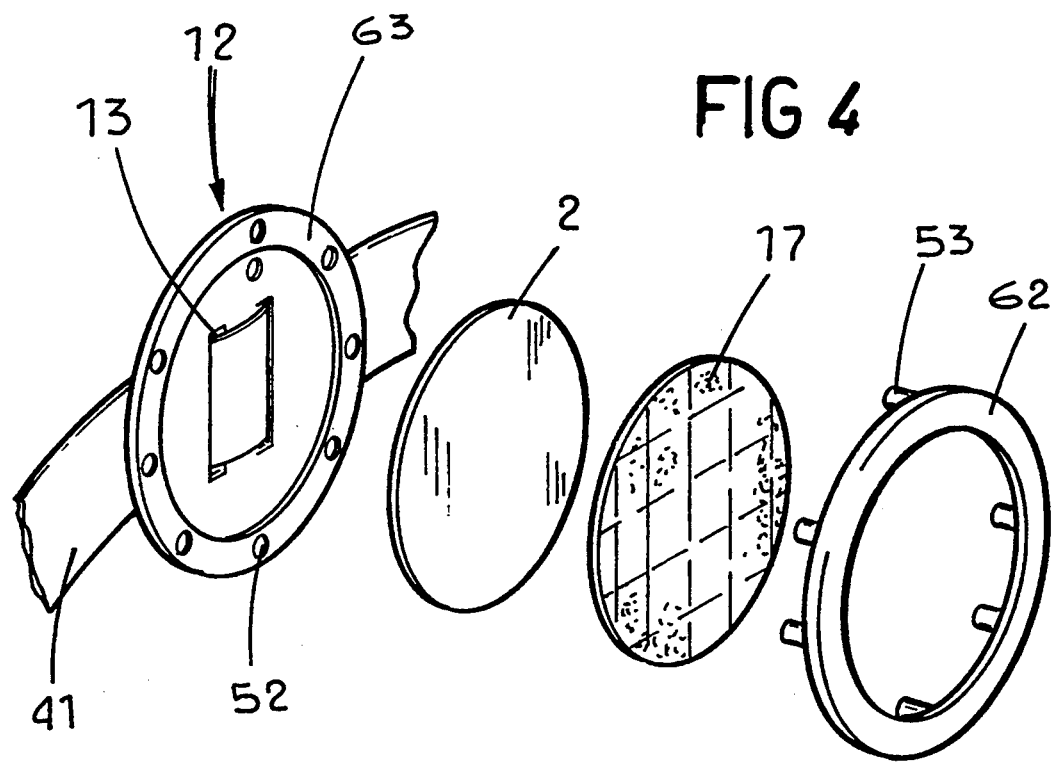
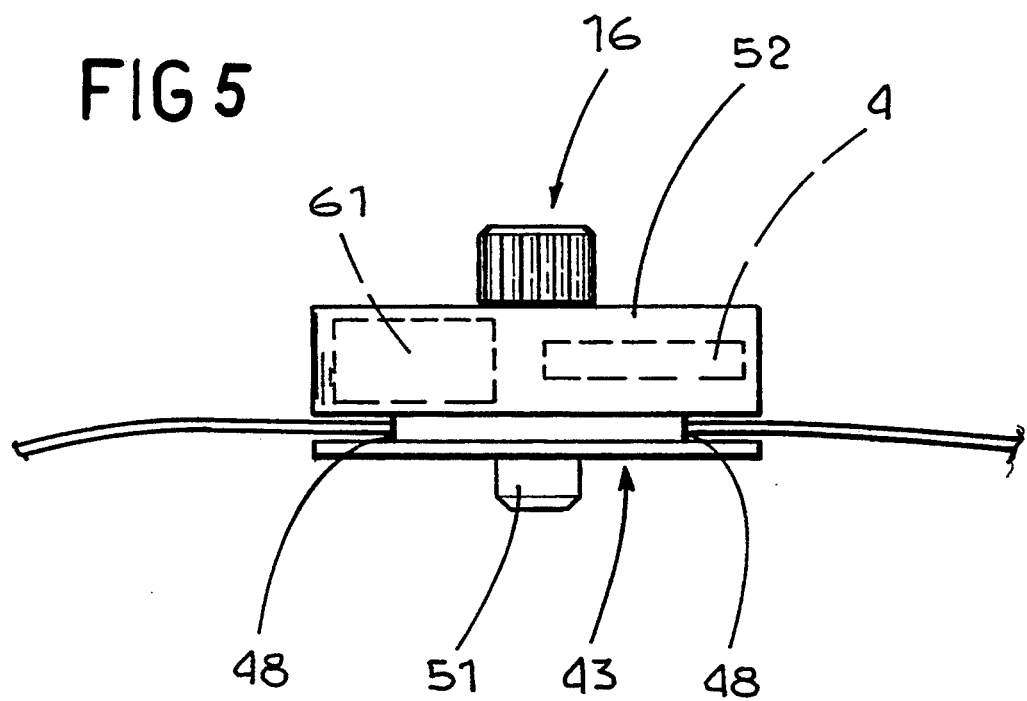

SUPPORT FOR BEARING AND POSITIONALLY ADJUSTING ELECTRODES OF PORTABLE BELT DEVICES FOR PASSIVE GYMNASTICS

BACKGROUND OF THE INVENTION

The invention relates to a support for bearing and positionally adjusting electrodes of portable belt devices for passive gymnastics, in which the electrodes are placed in contact with the skin in such a way as to transmit electric impulses produced by a current generator to it.

The said impulses, as is known, cause the involuntary and rhythmic contractions of the muscle subject to the impulses, with benefits for the treated part in the form of muscle toning and shaping.

Prior art portable devices substantially envisage a belt, which the user can wear, slidably bearing a series of electrodes on a longitudinal guide interconnected to the said belt. The said electrodes are destined to come into contact with the skin.

The movement of the electrodes along the guide is permitted by the fact that they are connected to the current generator by means of conductors of adequate length. The conductors are contained within a special pocket internally of the belt, which houses the conductors together with the necessary supply battery.

The fundamental drawback of such prior art devices is that the electrodes are positionable along the sliding guide only longitudinally to the belt.

The said devices, therefore, can be used correctly for treatment of the abdomen and the gluteus, but do not permit rational treatment of muscles which are arranged transversally to the wrap-round lines of the belt, such as, for example, in the case of limb muscles.

It is indeed clear that in the case of limb muscles, a correct stimulation could be had only by arranging the belt longitudinally, compatibly with the development of the muscle bundles, but in such a case it would be necessary to forego the full closure of the belt, with the disadvantages in terms of comfort and efficiency that such a contingency would necessarily incur.

SUMMARY OF THE INVENTION

An aim of the present invention, as it is characterised in the claims, is that of obviating the above-mentioned drawbacks. The invention attains the said aim by means of a support, applicable to a belt device for passive gymnastics in which the electrodes are placed in contact with the skin in such a way as to transmit electric impulses to the skin, which impulses are produced by a current generator, comprising a support element of the electrodes which projects from the belt, the said support element being rotatably interconnected with the device in such a way as to rotate with respect to the belt, enabling a couple of electrodes to be positioned longitudinally or transversally to the device itself, correspondingly to the development of the muscle bundle to be subjected to stimulation.

The support element of the electrodes has a curved profile, with its concavity turned towards the skin, so that when an electrode is placed in contact with the part to be treated, and the belt device is closed, the support element elastically contrasts the electrodes, pressing them on to the skin and opposing their accidental detachment therefrom.

The fundamental advantage of the invention essentially consists in the possibility of correctly and comfortably involving a wider range of parts of the body in passive gymnastics, independently of muscle direction with respect to the attachment line of the belt device.

A further advantage of the invention is represented by its easy dismounting and remounting, enabling easy cleaning and maintenance.

A still further advantage of the invention lies in the fact that its tension generator and relative battery can be contained in a cavity made in an element which is a component of the support. This contributes considerably to reducing the costs and complexity of the entire belt device to which the support is applied, also permitting the realisation of belt devices for passive gymnastics which are more compact, and thus suitable for the treatment of smaller areas of the human anatomy or parts of the body such as wrists, ankles etc.

BRIEF DESCRIPTION OF THE DRAWINGS

Further characteristics and advantages of the present invention will better emerge from the detailed description that follows, together with the accompanying drawings which represent a preferred but not exclusive embodiment and in which:

FIG. 1 shows, in a perspective view of the entirety of the invention, a belt device for passive gymnastics to which a support according to the invention is fitted;

FIG. 2 shows the invention represented according to a frontal view of its entirety;

FIG. 3 shows the invention of FIG. 2 in an exploded plan view;

FIG. 4 shows, in an exploded perspective view, an electrode applied to a support made according to the invention;

FIG. 5 shows a particular of the invention represented in enlarged scale, in one of its alternative embodiments.

DESCRIPTION OF THE PREFERRED EMBODIMENTS

With reference to the accompanying drawings, FIG. 1 shows a belt 1 device 50 to be worn for passive toning and shaping gymnastics, equipped with a generator 4 of current which is electrically interconnected with electrodes 2 destined to operate in direct contact with the skin in such a way as to transmit to it electrical impulses of appropriate characteristics.

The belt 1 is made of highly-deformable plastic material and exhibits at its opposite ends 60 velcro elements 7 reciprocally superimposable and forming together an length-adjustable closing device according to the requirements of the user.

The current generator 4 is contained, together with an autonomous battery 61, internally to a pocket 3 made internally to the belt 1 and is accessible through an opening 31 hidden by a fold 32.

The belt 1 further comprises a panel 15 equipped with a command knob 16 for the activation and positional adjustment of the electrodes 2 on the skin.

The support 40 comprises a projecting support element 41, projecting towards the user's skin and supporting a pair of electrodes 2 slidably interconnected with the support element 41 so as to be slidable with respect to the said support element 41, as is indicated in FIG. 3.

Indeed, with reference also to FIG. 4, it can be observed that the electrodes 2, of known type, comprise their own supports 12 equipped with grooves 13 destined to associate slidably with the projecting support element 41. The supports 12 are made in two semiparts 62, 63 reciprocally frontally and movably associable, by means of pins 53 borne on a first semipart 62, frontally insertably in corresponding cavities 52 made in the second semipart 63.

The electrode 2 is covered with a tract of sponge 17 turned towards the skin, and is also interpositioned between the semiparts 62, 63, of the supports 12, destined to be coated with an electricity-conducting conductor.

The support element 41 of the electrodes 2 is made of deformable plastic material, but has a greater rigidity than the belt 1 material. It is further equipped, at its ends 46 (see FIG. 3) with transversal strikers 47 to limit the sliding of the electrodes 2 with respect to the projecting support element 41 itself.

The said projecting support element 41 is further rotatably interconnected, at its halfway point 45, (see FIGS. 1 and 3), to the belt 1 device 50 in such a way as to rotate about the said device 50 and permit the electrode pair 2, arranged bilaterally to the said halfway point 45 to be longitudinally or transversally positioned with respect to the device 50 and correspondingly to the development of the muscle bundle to be subjected to electrical stimulation.

With reference to FIGS. 3 and 5, it can be observed that the support 40 preferably comprises also a longitudinal sliding element 43, longitudinally sliding with respect to the belt 1, pierced by a hole 48 shaped complementarily to the guide 14 itself.

In the above case the projecting support element 41 of the electrodes 2 is rotatably interconnected to the longitudinal sliding element 43, so that the combination of the longitudinal sliding element 43 sliding possibilities along the guide 14, and the rotatable connection between the longitudinal sliding element 43 and the projecting support element 41 of the electrodes 2 confers on the said electrodes 2 a rotating-sliding ability with respect to the device 50.

The connection of the projecting support element 41 to the longitudinal sliding element 43 is preferably realised (see FIGS. 3 and 5) by means of a pivot 42, projectingly supported by the projecting support element 41 of the electrodes 2, and elastically snap-on fitted in a corresponding hinge 51 complementarily shaped, made in the longitudinal sliding element 43.

With reference to FIG. 3, it can be observed that the projecting support element 41 of the electrodes 2 preferably exhibits an arcuate shape or a curved profile having, when the belt 1 device 50 is worn, its concavity turned towards the skin. This advantageously allows a contrasting elastic pressure of the electrodes 2 against the skin and ensures the said electrodes 2 positional stability well as the continuity of the electrical current.

In an alternative embodiment of the invention, represented in FIG. 5, the support 40 can be conformed in such a way as advantageously to incorporate also the generator 4 of current for the electrodes 2 and the relative battery 61, in a special cavity 52 made in the longitudinal sliding element 43.

From this the possibility derives of considerably simplifying the structure of the belt 1 device 50. FIGS. 3 and 5 show that by equipping the guide 14 with an adjustable closing device, for example of the type similar to that constituted by the velcro elements 7 applied to the ends 60 of the belt 1, it is possible to realise a low-cost belt device 50, advantageously applicable to the treatment of small parts of the human anatomy, such as wrists, ankles etc.

What is claimed is:

1. A device for bearing and positionally adjusting electrodes of a portable belt for passive gymnastics, wherein the electrodes transmit electric pulses to a person wearing the belt, the device comprising a belt at least an arcuate shaped support element having opposing end portions, each end portion supporting an electrode, an intermediate portion of said arcuate shaped support element rotatably coupled to an inner surface of the belt, a concavity of the arcuate shaped support element turned inward from the inner surface of the belt so as to be toward the person wearing the belt so that the electrodes project towards the person wearing the belt, wherein the arcuate shaped support element maintains the electrodes in contact with the person wearing the belt.

2. The device of claim 1, further comprising an electrode support element supporting one of the electrode, said electrode support element slidably disposed on the arcuate shaped support element, wherein the electrode supported by the slidable electrode support element is positionable in relation to said arcuate shaped support element and the belt.

3. The device of claim 2, further comprising a striker disposed on at least one of the end portions of said arcuate shaped support element, wherein said striker limits the positioning of the electrode supported by the slidable electrode element in relation to said arcuate shaped support element.

4. The device of claim 1, further comprising a guide disposed along a longitudinal dimension on the inner surface of the belt, and a sliding element slidably engaged to said guide, wherein said sliding element is slidable, in the longitudinal dimension, in relation to the belt, said arcuate shaped support element being rotatably coupled to said sliding element, wherein said arcuate shaped support element is rotatable in relation to the belt, and slidably positionable in relation to the belt.

5. The device of claim 4, further comprising a hinge disposed on said sliding element, and a pivot disposed on said arcuate shaped support element, said pivot of said arcuate shaped support element being elastically snap-couplable to said hinge on said sliding element, wherein said arcuate shaped support element is removable from the belt.

6. The device of claim 4, further comprising a shaped hole extending through said sliding element, said guide extending through said shaped hole in said sliding element.

7. The device of claim 4, further comprising an internal cavity disposed in said sliding element.

8. The device element of claim 1, wherein the arcuate shaped support element is formed of a deformable plastic material.

* * * * *

UNITED STATES PATENT AND TRADEMARK OFFICE
CERTIFICATE OF CORRECTION

PATENT NO. : 5,443,494

DATED : August 22, 1995

INVENTOR(S) : Paolizzi, Marco & Valentini, Marco

It is certified that error appears in the above-indentified patent and that said Letters Patent is hereby corrected as shown below:

On the title page, insert item [73],

Assignee: Vupiesse Italia S.A.S. Di Valentini E Paolizzi E.C., Rimimi, Italy

Signed and Sealed this

Ninth Day of January, 1996

Attest:

BRUCE LEHMAN

Attesting Officer

Commissioner of Patents and Trademarks